United States Patent [19]

Uskokovic

[11] Patent Number: 5,258,559
[45] Date of Patent: Nov. 2, 1993

[54] **PROCESS FOR THE PREPARATION OF [1R-(1β(R*), 3Aα, 4β, 7Aβ)] OCTAHYDRO-1-(5-HYDROXY-1,5-DIMETHYLHEXYL)-7A-METHYL-4H-INDEN-4-ONE**

[75] Inventor: Milan R. Uskokovic, Upper Montclair, N.J.

[73] Assignee: Hoffmann-La Roche Inc., Nutley, N.J.

[21] Appl. No.: 889,031

[22] Filed: May 26, 1992

Related U.S. Application Data

[63] Continuation of Ser. No. 715,940, Jun. 14, 1991, abandoned, which is a continuation of Ser. No. 619,167, Nov. 27, 1990, abandoned.

[51] Int. Cl.⁵ .................................................. C07C 45/64
[52] U.S. Cl. ...................................... 568/343; 568/363
[58] Field of Search .................................. 568/363, 363

[56] References Cited

U.S. PATENT DOCUMENTS

| | | | |
|---|---|---|---|
| 3,646,149 | 2/1972 | Morel | 568/363 |
| 3,790,635 | 2/1974 | Morel | 568/363 |
| 4,209,450 | 6/1980 | Jaedicke et al. | 568/363 |
| 4,804,502 | 2/1989 | Baggiolini et al. | 260/377.2 |

FOREIGN PATENT DOCUMENTS

| | | | |
|---|---|---|---|
| 341158 | 11/1989 | European Pat. Off. | 260/397.2 |
| 2633613 | 5/1990 | France | 568/363 |

OTHER PUBLICATIONS

Kiersznicki et al., Chem. Abst., vol. 103, #71612g (1985).
Carlsen, Synth. Commun, vol. 17, pp. 19–23 (1987).
Inhoffen et al., Chem. Ber., vol. 90, p. 664 (1957).
Tetrahedron Letters 32, 6057–6060 (1991) Kiegel, Wovkulich, Uskokovic J. Org. Chem. vol. 51, No. 16, 1986, pp. 3100–3101.
Tenaglia et al., Ruthenium Catalyzed C—H Bond Activation Oxidation of Bridged Bicyclic and Tricyclic Alkanes, Tetrahedron Letters, vol. 30, No. 39 pp. 5271–5274 (1989).
Abstract Corresponding to French 2633613.

*Primary Examiner*—James H. Reamer
*Attorney, Agent, or Firm*—George M. Gould; George W. Johnston; Ellen Ciambrone Coletti

[57] ABSTRACT

A process for the preparation of [1R-(1β(R*),3aα,4α,-7aβ)]octahydro-1-(5-hydroxy-1,5-dimethyl(hexyl)-7a-methyl-4H-inden-4-one which comprises reacting [1R-(1β(R*)3aα,7aβ)]octahydro-1-(1,5-dimethylhexyl)-7a-methyl-4H-inden-4-ol or [1R-(1β(R*) 3aα,7aβ)]octahydro-1-(1,5-dimethylhexyl)-7a-methyl-4H-inden-4-one with sodium metaperiodate and ruthenium chloride hydrate.

10 Claims, No Drawings

PROCESS FOR THE PREPARATION OF [1R-(1β(R*), 3Aα, 4β, 7Aβ)] OCTAHYDRO-1-(5-HYDROXY-1,5-DIMETHYL-HEXYL)-7A-METHYL-4H-INDEN-4-ONE

This is a continuation of application Ser. No. 07/715,940 filed Jun. 14, 1991, now abandoned which is a Rule 60 continuation of Ser. No. 07/619,167, filed Nov. 27, 1990, abandoned.

BACKGROUND OF THE INVENTION

The known methods of preparing [1R-(1β(R*),3aα,4β,7aβ)] octahydro-1-(5-hydroxy-1,5-dimethyl hexyl)-7a-methyl-4H-inden-4-one, include that set forth in J. Org. Chem., Vol. 51, No. 16, 1986 p. 3100-3101. In particular, that process comprises a multiple step process which involves tosylating a compound of the formula

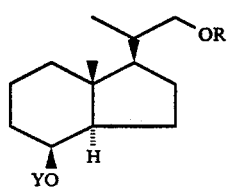

wherein R is hydrogen and Y is silyl, reacting the resulting product with the lithium derivative of 3-methyl-1-butyn-3-yl tetrahydropyranyl ether in refluxing dioxane, followed by catalytic hydrogenation of the acetylenic moiety over rhodium on charcoal, removal of the alcohol protecting group and oxidation with pyridinium chlorochromate to yield, for example, [1R-(1β(R*),3aα, 4β, 7aβ)] octahydro-1-(5-hydroxy-1,5-dimethylhexyl)-7a-methyl-4H-inden-4-one.

BRIEF SUMMARY OF THE INVENTION

The invention relates to a process for the preparation of [1R-(1β(R*),3aα,4β, 7aβ)]octahydro-1-(5-hydroxy-1,5-dimethylhexyl)-7a-methyl-4H-inden-4-one, characterized by the formula

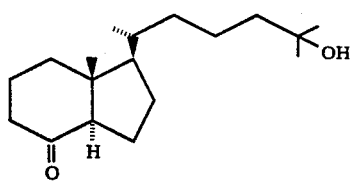

which comprises reacting the compound of the formula

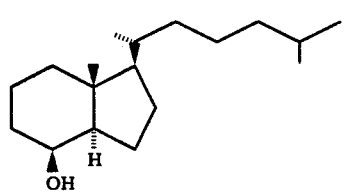

with sodium metaperiodate and ruthenium chloride hydrate.

In another aspect, the invention relates to a process for the preparation of the compound of Formula I which comprises reacting the compound of the formula

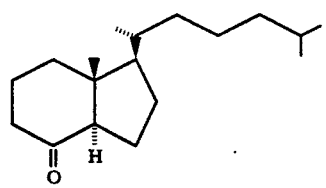

with sodium metaperiodate and ruthenium chloride hydrate.

DETAILED DESCRIPTION OF THE INVENTION

In the formulas represented herein, when substituents are illustrated as joined to the nucleus by a solid line (———), indicates that the substituent is in the β-orientation, that is, above the plane of the molecule, a broken line (⊪⊪⊪⊪), indicates that the substituent is in the α-orientation, that is, below the plane of the molecule.

The invention relates to the preparation of [1R-(1β(R*),3aα, 4β, 7aβ)]octahydro-1-(5-hydroxy-1,5-dimethylhexyl)-7a-methyl-4H-inden-4-one, characterized by the formula

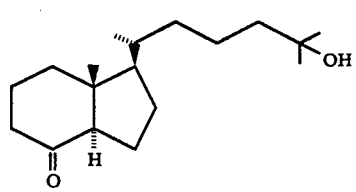

More particularly, the invention relates to a process for the preparation of the compound of Formula I which comprises reacting [1R-(1β(R*),3aα,7aβ)]octahydro-1-(1,5-dimethylhexyl)-7a-methyl-4H-inden-4-ol, characterized by the formula

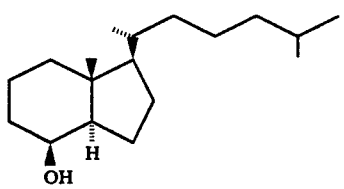

with sodium metaperiodate and ruthenium chloride hydrate to yield a mixture of compounds of the formulas

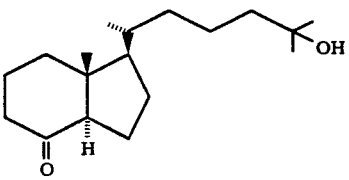

and

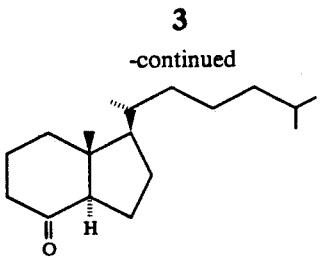

III

-continued and thereafter separating the resulting products of formulas I and III by flash chromatography or the like.

In accordance with the invention, the alcohol of formula II, which is a known compound disclosed in Inhoffen. H. H.; Quinkert, G.; Schutz, S; Kampe, D; Domagk, G; F. Chem. Ber. 1957,90.664, is reacted with ruthenium (III) chloride hydrate and sodium metaperiodate to yield compounds of formulas I and III. The reaction is carried out in a mixture of a chlorinated organic solvent, for example, methylene chloride, carbon tetrachloride, or the like, and a nitrile, for example, acetonitrile, or the like, preferably, a mixture of carbon tetrachloride and acetonitrile, in the presence of a buffering agent, for example, monobasic potassium phosphate-sodium hydroxide in water, which adjusts the pH of the solution in the range of from 6 to 8, preferably to a pH of 7. The reaction is carried out at a temperature in the range of from about 0° to about 60° C., preferably in the range of from about 40° C. to about 50° C., more preferably at 45° C. After stirring, water is added and the solution is extracted by conventional means, such as, for example, with methylene chloride. The extracts are dried by conventional means, for example, over magnesium sulfate and evaporated. The compounds of Formulas I and III can be separated by conventional methods, for example, by flash chromatography or the like.

The compound of Formula I can also be prepared by converting the compound of Formula III obtained above to the compound of Formula I. More particularly, the compound of Formula III, [1R-(1β(R*),3aα, 7aβ)]octahydro-1-(1,5-dimethyl-hexyl)-7a-methyl-4H-inden-4-one, is reacted with ruthenium (III) chloride hydrate and sodium metaperiodate in a mixture of a chlorinated organic solvent, for example, methylene chloride, carbon tetrachloride or the like, and a nitrile, for example, acetonitrile or the like, preferably, in a mixture of carbon tetrachloride and acetonitrile, in the presence of a buffering agent, for example, monobasic potassium phosphate-sodium hydroxide in water, which adjusts the pH of the solution in the range of from 6 to 8, preferably to a pH of 7. The reaction is carried out in a temperature in the range of from about 0° C. to about 60° C., preferably in the range of from about 40° C. to about 50° C., preferably at about 45° C. After stirring, water is added and the solution is extracted by conventional means, for example, with methylene chloride. The extracts are dried by conventional means, for example, over magnesium sulfate, and evaporated. The compound of formula I is recovered from the reaction mixture by conventional methods, for example, by flash chromatography or the like.

The compound of Formula I is a known precursor for the preparation of 1α,25-dihydroxycholecalciferol and thus is useful in the synthesis of 1α,25-dihydroxycholecalciferol, see for example, J. Org. Chem., Vol. 51, No. 16, 1986. It is well known that 1α,25-dihydroxycholecalciferol plays a central role in the maintenance of the calcium and phosphorus homeostasis in the blood plasma and in the induction of mineralization and calcium mobilization of the bones. Also, 1α,25-dihydroxycholecalciferol is useful in the treatment of psoriasis.

The Examples which follow further illustrate the invention. All temperatures are given in degrees Celsius.

EXAMPLE 1

Preparation of [1R-(1β(R*),3aα,4β,7aβ)] octahydro-1-(5-hydroxy-1,5-dimethylhexyl)-7a-methyl-4H-inden-4-one

[1R-(1β(R*),3aα,7aβ)] octahydro-1-(1,5-dimethylhexyl)-7a-methyl-4H-inden-4-ol (2.66 g, 0.01 mol) (prepared as described in Inhoffen et al., F. Chem. Ber. 1957, 90.664), sodium metaperiodate (7.48 g), ruthenium (III) chloride hydrate (0.207 g, 10 mol %), carbon tetrachloride (40 ml), acetonitrile (40 ml) and pH 7.0 buffer (monobasic potassium phosphate-sodium hydroxide, 0.05M in water) (52 ml) were stirred vigorously by mechanical stirring for 68 hours at 45° C. After this period, 30 ml water was added and this was extracted with methylene chloride (2×40 ml). The extracts were combined, dried over magnesium sulfate and evaporated. Flash chromatography (hexanes −EtOAc=20:1, later 4:1) afforded 0.73 g (26%) of [1R-(1β(R*), 3aα, 7aβ)]octahydro-1-(1,5-dimethylhexyl)-7a-methyl-4H-inden-4-one, the compound of formula III, and 1.15 g (41%) of [1R-(1β(R*), 3aα, 4β, 7aβ)]octahydro-1-(5-hydroxy-1,5-dimethylhexyl)-7a-methyl-4H-inden-4-one, the compound of formula I, as a pale yellow oil which solidifies upon standing in the freezer.

EXAMPLE 2

Preparation of [1R-(1β(R*),3aα,4β 7aβ)] octahydro-1-(5-hydroxy-1,5-dimethylhexyl)-7a-methyl-4H-inden-4-one

[1R-(1β(R*),3aα,7aβ)] octahydro-1-(1,5-dimethylhexyl)-7a-methyl-4H-inden-4-one (23.3 g), sodium metaperiodate (47.11 g), ruthenium (III) chloride hydrate (1.83 g, 10 mol %), carbon tetrachloride (350 ml), acetonitrile (350 ml) and pH 7.0 buffer (monobasic potassium phosphate-sodium hydroxide, 0.05M in water) (530 ml) were stirred vigorously by mechanical stirring for 60 hours at 45° C. After this period, water (300 ml) was added and this was extracted with methylene chloride (2×400 ml). The extracts were combined, dried over magnesium sulfate and evaporated. Flash chromatography (hexane-ethylacetate=20:1, later 4:1) afforded 6.89 g (29.4%) of starting material [1R-(1β(R*),3aα, 7aβ)-]octahydro-1-(1,5-dimethylexyl)-7a-methyl-4H-inden-4-one, and 9.54 g (38.6%) of [1R-(1β(R*), 3aα, 4β, 7aβ)]octahydro-1-(5-hydroxy-1,5-dimethylhexyl)-7a-methyl-4H-inden-4-one, the compound of formula I, as a pale yellow oil which solidifies upon standing in the freezer.

I claim:

1. A process for the preparation of [1R-(1β(R*),3aα,4β, 7aβ)]octahydro-1-(5-hydroxy-1,5-dimethylhexyl)-7a-methyl-4H-inden-4-one which comprises reacting a compound of the formula

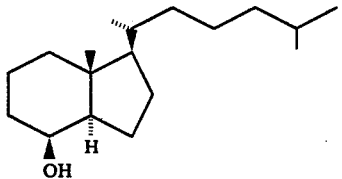  II with sodium metaperiodate and ruthenium chloride hydrate.

2. A process in accordance with claim 1, wherein a buffering agent is present.

3. A process in accordance with claim 2, wherein the buffering agent is monobasic potassium phosphate-sodium hydroxide.

4. A process in accordance with claim 3, wherein the reaction is carried out at a pH in the range of from about 6 to about 8.

5. A process in accordance with claim 4, wherein the reaction is carried out at a temperature in the range of from about 0° C. to about 60° C.

6. A process for the preparation of [1R-(1β(R*) 3aα, 4β, 7aβ)]octahydro-1-(5-hydroxy-1,5-dimethylhexyl)-7a-methyl-4H-inden-4-one which comprises reacting a compound of the formula

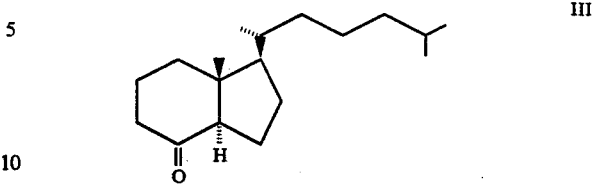  III with sodium metaperiodate and ruthenium chloride hydrate.

7. A process in accordance with claim 6, wherein a buffering agent is present.

8. A process in accordance with claim 7, wherein the buffering agent is monobasic potassium phosphate-sodium hydroxide.

9. A process in accordance with claim 8, wherein the reaction is carried out at a pH in the range of from about 6 to about 8.

10. A process in accordance with claim 9, wherein the reaction is carried out at a temperature in the range of from about 0° C. to about 60° C.

* * * * *